(12) United States Patent
Descargues et al.

(10) Patent No.: US 12,158,463 B2
(45) Date of Patent: Dec. 3, 2024

(54) EX VIVO SUBCUTANEOUS INJECTION MODEL

(71) Applicant: GENOSKIN, Toulouse (FR)

(72) Inventors: Pascal Descargues, Cambridge, MA (US); Emeline Pagès, Castanet Tolosan (FR); Claire Jardet, Cugnaux (FR)

(73) Assignee: GENOSKIN, Toulouse (FR)

( * ) Notice: Subject to any disclaimer, the term of this patent is extended or adjusted under 35 U.S.C. 154(b) by 940 days.

(21) Appl. No.: 16/971,599

(22) PCT Filed: Mar. 3, 2019

(86) PCT No.: PCT/EP2019/000061
§ 371 (c)(1),
(2) Date: Aug. 20, 2020

(87) PCT Pub. No.: WO2019/170281
PCT Pub. Date: Sep. 12, 2019

(65) Prior Publication Data
US 2020/0400652 A1  Dec. 24, 2020

(30) Foreign Application Priority Data
Mar. 5, 2018  (FR) ........................... 1870232

(51) Int. Cl.
G01N 33/50 (2006.01)
C12M 1/12 (2006.01)
C12M 3/00 (2006.01)
C12N 5/071 (2010.01)

(52) U.S. Cl.
CPC ......... *G01N 33/5082* (2013.01); *C12M 21/08* (2013.01); *C12M 25/04* (2013.01); *C12N 5/0698* (2013.01); *C12N 2500/14* (2013.01); *C12N 2533/76* (2013.01)

(58) Field of Classification Search
None
See application file for complete search history.

(56) References Cited

U.S. PATENT DOCUMENTS

2014/0271508 A1* 9/2014 Florence ............... A61Q 19/06
424/195.17
2015/0132737 A1* 5/2015 Descargues ........ G01N 33/5044
435/284.1

FOREIGN PATENT DOCUMENTS

| EP | 3 256 568 | 12/2017 |
| EP | 2 882 290 | 8/2019 |
| WO | 2012/059703 | 5/2012 |
| WO | 2013/164436 | 11/2013 |

OTHER PUBLICATIONS

ICH Expert Working Group, ICH Harmonised Tripartite Guideline, "Specifications: Test Procedures and Acceptance Criteria for New Drug Substances and New Drug Products: Chemical Substances Q6A," International Conference on Harmonisation of Technical Requirements for Registration of Pharmaceuticals for Human Use, Oct. 6, 1999, 35 pages.
Howard et al., "A New Method for the Establishment of Diploid Fibroblast Cell Cultures from Human Foreskins (39528)," Proceedings of the Society for Experimental Biology and Medicine, vol. 153, 1976, pp. 280-283.
Written Opinion of the International Searching Authority issued in International Application No. PCT/EP2019/000061 dated Apr. 23, 2019 with English translation provided.
De Wever et al. "Human Skin Models for Research Applications in Pharmacology and Toxicology: Introducing NativeSkin®, the "Missing Link" Bridging Cell Culture and/or Reconstructed Skin Models and Human Clinical Testing," Applied In Vitro Toxicology, vol. 1, No. 1, 2015, pp. 26-32.
Park et al., "Usefulness of Skin Explants for Histologic Analysis after Fractional Photothermolysis," Annals of Dermatology, vol. 27, No. 3, 2015, pp. 283-290.
Lebonvallet et al., "The evolution and use of skin explants: potential and limitations for dermatological research," European Journal of Dermatology, vol. 20, No. 6, Nov.-Dec. 2010, 14 pages.
International Search Report for PCT/EP2019/000061 dated Apr. 23, 2019, 7 pages, with English Translation.
Written Opinion of the ISA for PCT/EP2019/000061 dated Apr. 23, 2019, 6 pages.

* cited by examiner

*Primary Examiner* — Teresa E Knight
(74) *Attorney, Agent, or Firm* — NIXON & VANDERHYE

(57) ABSTRACT

Disclosed is an ex vivo model for subcutaneous injection and aims at providing an in vitro method including the steps of i) immersing a skin explant in a solidifiable liquid matrix such that the upper face of the epidermis is not covered, which matrix is itself contained in a cell culture insert, the bottom of which consists of a porous membrane, and (ii) solidifying this matrix so as to trap the immersed portion of this skin explant, wherein the upper face of the epidermis is not covered, and adhering this same matrix to the side walls and the porous membrane of the insert, wherein the skin explant includes a thickness of at least 5 mm of hypodermis.

5 Claims, 5 Drawing Sheets

EX VIVO SUBCUTANEOUS INJECTION MODEL

CROSS-REFERENCE TO RELATED APPLICATIONS

This application is the U.S. national phase of International Application No. PCT/EP2019/000061 filed Mar. 3, 2019 which designated the U.S. and claims priority to French Application No. 1870232 filed Mar. 5, 2018, the entire contents of each of which are hereby incorporated by reference.

FIELD OF THE INVENTION

The present invention relates to the field of subcutaneous injection and provides, more specifically, the first ex vivo model for this type of injection.

PRIOR ART

Syringeability and injectability are two critical characteristics of any formulation intended for parenteral injection. The first refers to the ability of a formulation to pass easily through a hypodermic needle, and the second refers to the performance of that formulation during injection (GROVES, Parenteral Technology Manual. Interpharm Press. Vol. 9, p:99-100, 1988).

Syringeability is based on various factors such as ease of clogging, foaming, or measuring the dose to be injected. As for injectability, it is based on the required injection pressure or force, uniformity of flow, and absence from clogging.

These two parameters can be affected both by the formulation itself and by the geometry of the needle, especially by its internal diameter, by its length, by the shape of the opening, or by the tip of the syringe. These two parameters are in any case of critical importance when dealing with self-injection devices, such as pens or auto-injectors, which are equipped with very fine needles, with needles in the range of 29 to 31 G. While such needles may reduce injection pain, they nevertheless require an increase in injection force and therefore require rapid determination of the syringeability and injectability of the composition during development so that they can be modified if necessary.

According to ICH guideline Q6A (INTERNATIONAL CONFERENCE ON HARMONISATION OF TECHNICAL REQUIREMENTS FOR REGISTRATION OF PHARMACEUTICALS FOR HUMAN USE), parenteral formulations packaged in pre-filled syringes or in auto-injector cartridges should be subject to test procedures and acceptance criteria related to the functionality of the delivery system. Similarly, in the FDA's guidance for industry on container closure systems for packaging human drugs and biological products, evaluation of syringe performance is required. These prerequisites should be addressed by determining the force required to initiate and maintain the movement of the plunger in the chamber, and the ability of the syringe to deliver the quantity of drug product.

Despite these regulatory requirements, no formal testing procedures are specified in the pharmacopoeias. Now, while poor syringeability can be easily solved by varying the needle size, the same cannot be said for injectability. Therefore, since injectability potentially has a significant impact on patient compliance, it is important to study this parameter at an early stage.

Methods for determining the injectability of a composition have therefore been determined in the prior art. RITSCHEL & SUZUKI (1979) thus proposed a method for determining the injectability of parenteral compositions based on the determination of the time required for the gentle injection, at a given pressure and for a given needle-syringe system, of a given solution or suspension in a meat sample. Determining the force required to inject a liquid through a needle has in the past also used a dynamometer or a micro-capillary rheometer connected to a dynamometer. Finally, studies conducted with these devices have shown that the injectability of a composition is linked, on the one hand, to the speed of its injection and its viscosity, and, on the other hand, to the nature of the medium into which it is injected. As a result, the determination and adaptation of the in vivo (in the skin) injectability of a given composition are not easily accessible and usually require a final testing step in humans.

There is therefore an existing need to easily and quickly determine the in vivo injectability of a composition, particularly by subcutaneous route, limiting, as far as possible, the need for development (reformulation) in humans, but also the need for animals, given that their use tends to be increasingly limited.

SUMMARY OF THE INVENTION

Indeed, the inventors have demonstrated that despite the "soft" structure of the hypodermis, the use of a skin explant comprising at least 5 mm of hypodermis in a specific culture method does not, as might have been expected, cause the hypodermis to become sluggish over time. It is also common that the loss of the three-dimensional structure leads to functional changes and modification of the cell structure with, in particular, dedifferentiation or inappropriate differentiation phenomena. On the contrary, the inventors were able to demonstrate that such a skin explant used in this culture method retains its native three-dimensional structure where the connective tissue as well as the adipocyte tissue forming the hypodermis do not show any change over time, especially at the cellular level. It is thus possible, after 5 to 7 days, to make a skin fold on the latter in order to carry out a subcutaneous injection.

This discovery makes it possible to benefit from a cultured skin explant faithfully reproducing ex vivo the three-dimensional structure of the skin with its different layers, especially its hypodermis. Therefore, the existence of such an explant makes it possible, for the first time, to test ex vivo a subcutaneous injection and its various parameters. This discovery by the inventors led to the development of the first ex vivo model for subcutaneous injection, which model faithfully reproduces the three-dimensional structure of the skin, even after several days of culture.

Accordingly, a first object of the invention relates to an in vitro method comprising the steps of:
i) immersing a skin explant in a solidifiable liquid matrix such that the upper face of the epidermis is not covered, which matrix is itself contained in a cell culture insert, the bottom of which consists of a porous membrane, and
ii) solidifying this matrix so as to trap the immersed portion of this skin explant, wherein the upper face of the epidermis is not covered, and adhering this same matrix to the side walls and the porous membrane of the insert;
characterized in that the skin explant comprises a thickness of at least 5 mm of hypodermis and in that the method aims at obtaining an ex vivo model for subcutaneous injection.

Advantageously, the method according to the invention further comprises the steps of:

iii) placing the insert in a container or culture well, and
iv) culturing the skin explant in an appropriate medium.

A second object of the invention relates to a cell culture insert obtainable by the method according to the invention, which can be placed in a container or culture well, which has a bottom consisting of a porous membrane, and which contains the skin explant trapped in a solidified matrix which is in contact with the inner edge of the insert and the porous membrane, and wherein the epidermis of the skin explant is in contact with the atmosphere, and the dermis, epidermal appendages, and hypodermis of this skin explant are trapped in the solidified matrix.

It should be noted that this insert constitutes the ex vivo model for subcutaneous injection obtained by the method according to the invention.

A third object of the invention relates to the use of such an insert as an ex vivo model for subcutaneous injection.

Advantageously, for the determination of the injectability of a composition, the bolus of injection of the composition, with the local toxicity resulting from the injection of the composition and/or the efficacy of the composition A fourth object of the invention relates to a kit comprising such an insert and an automatic injection device, which is preferably coupled to a dynamometer, so as to be able to determine the injectability characteristics of a composition.

DETAILED DESCRIPTION OF THE INVENTION

Figure 1:
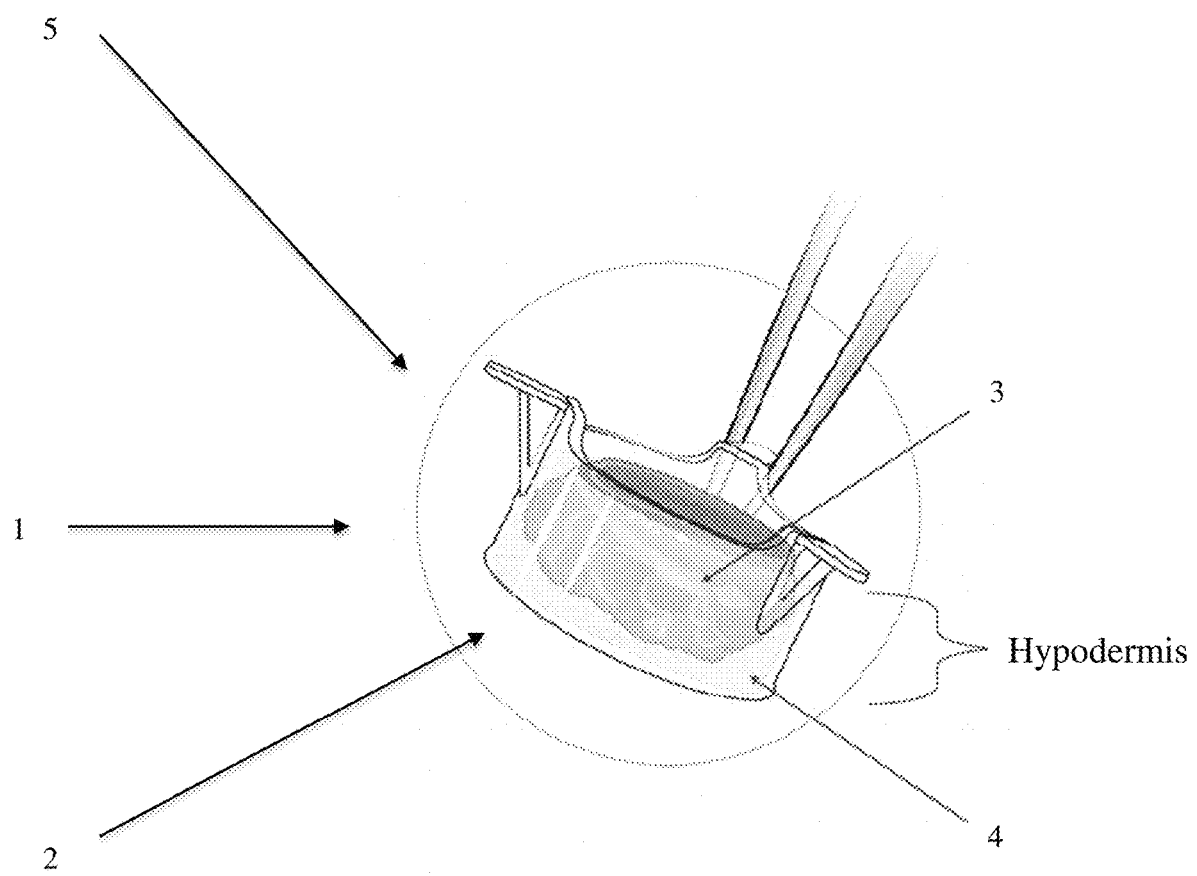
FIG. 1 is a representation of the cell culture insert (1) with lugs (5), the bottom of which consists of a porous membrane (2) and which contains the skin explant (3) trapped in a solidified matrix (4).

With respect to the first object of the invention, by "subcutaneous injection" is meant an injection that is carried out in the hypodermis, which is also referred to as a "hypodermic" injection. This type of injection, which is well known to the one skilled in the art, generally requires a skin fold to be made with the fingers and the subcutaneous injection is then performed in the skin fold.

By "skin explant" is meant a skin fragment that comprises, in addition to the epidermis, dermis, and epidermal appendages, a thickness of at least 5 mm of hypodermis. The epidermal appendages correspond to the hair follicles, sebaceous glands, and sweat glands. The hypodermis is the layer of tissue immediately below the dermis of the skin. The hypodermis is a loose connective tissue that is richly vascularized and also contains adipose tissue.

Ideally, the skin explant comprises between 5 and 15 mm of hypodermis and preferentially between 5 and 10 mm of hypodermis.

In connection with step i), the immersion of the skin explant is such that the hypodermis is completely immersed in the solidifiable liquid matrix and as for the upper layer of dermis, it is immersed to at least 90% (in the direction of the thickness), preferably to at least 95%, and ideally completely. At the same time, the epidermal layer, on the surface of the skin explant, emerges by at least 90% (in the direction of the thickness), preferably by at least 95% and, ideally again, completely.

As regards the solidification phase, it is carried out so that the exposure of the hypodermis, dermis, and epidermis is the same as following the phase of immersion of the skin explant in the solidifiable liquid matrix.

While the skin explant is advantageously cylindrical in shape, other geometrical shapes may be perfectly suitable for implementing the method according to the invention.

Thus, skin explants with square, rectangular, oval, triangular, or other shapes can be considered.

The dimensions of the skin explant should be selected so that a skin fold can be made, which is typically achieved with a fine clamp. Now, there is no absolute need to make a skin fold to carry out the subcutaneous injection. In the case of an automated subcutaneous injection device, for example, there is no need for such a skin fold, and this injection can be performed by setting the subcutaneous injection device so that it injects at a needle penetration depth into the explant that is previously set.

In the case of a cylindrical skin explant, a skin explant with a diameter between 10 mm and 50 mm, preferably between 15 mm and 40 mm, or even between 15 mm and 30 mm, with values typically ranging from 17 mm to 23 mm, should be used.

If this skin explant is taken from a mammal, the choice is between human or pig. Now, in view of the preferred destination of the method according to the invention, it will be best to use an explant of human skin.

In relation to the origin of the skin explant, it can come from a plasty from any part of the body, including plasties of the abdomen, chest, buttocks, back and even, why not, the scalp or any other part of the body with skin.

In order to benefit from a good survival of the skin explant in vitro, it is preferable that the skin explant be removed less than 72 h before its use in the method according to the invention. Now, an explant that was taken less than 48 hours ago is preferably used. Typically, once the skin explant has been taken, it takes at least one hour before it can be used in the method according to the invention.

Compared to the method described in international application WO 2013/164436, the method according to the invention of which constitutes, in a way, an improvement, the distinct nature of the skin explant used also makes it possible to dispense with the association of the skin explant with a ring (or perforated disc) consisting of a hydrophobic material and which will confer sufficient buoyancy to the explant within the liquid matrix.

Indeed, the inventors found that the presence of a thickness of at least 5 mm makes it possible to confer sufficient buoyancy to the skin explant on the liquid matrix so that no additional means need to be used to improve the buoyancy of the skin explant.

Consequently, and according to an embodiment which may be considered as preferred, the method according to the invention will not comprise any step, prior to step i), of fixing to the skin explant, in particular on the epidermal surface, a hydrophobic material; which hydrophobic material is normally used to improve the buoyancy of the skin explant.

Now, it is also possible to opt for such a preliminary step even if it is not necessary. Indeed, the fixation of this ring allows to delimit the area of topical application for compounds to be tested. In this case, the method according to the invention will then comprise, prior to the immersion of the skin explant in the solidifiable liquid matrix, a step i) of fixing to the surface of the epidermis of the skin explant a ring, or perforated disc, consisting of a hydrophobic material, the external diameter of which is greater than that of the epidermal surface of the skin explant, and the internal diameter of which is that of this same epidermal surface of the skin explant.

As a hydrophobic material that can be used to make this ring, materials that are not toxic to the skin are preferred, such as, for example, a paraffin polymer, such as PARAFILM® (SIGMA), or a silicone polymer.

As regards the fixation of this ring to the surface of the epidermis of the skin explant, it is preferably carried out by means of an adhesive, which adhesive is preferably added to the lower surface of the ring. This adhesive can be selected among any type of skin-harmless material and causing the ring to adhere to the epidermal surface of the skin explant. Typically, a hydrophobic adhesive such as, for example, a silicone-based adhesive, can be selected.

By "solidifiable liquid matrix" is meant any liquid solution, the specific composition of which (both in terms of compound(s) and concentration) is such that, when implementing suitable conditions, especially particular temperature conditions, the liquid solution takes on a solid- or gel-like consistency. Now, the nature of this solidifiable matrix must allow the skin biopsy cells to remain alive, that is to say not have any cytotoxic effect and have a solidification/polymerization temperature at room temperature (namely from 15° C. to 25° C.). Its specific composition can be of animal, vegetable, synthetic, or even mixed origin. In addition, the nature and concentration(s) of these components shall be selected according to the desired physicochemical characteristics of the matrix when solidified, in particular in terms of flexibility and strength. As regards the volume of the liquid matrix, it will be ⅓ to ⅔ of the total volume of the insert, preferably ⅖ to ⅗ of the total volume; with half of the total volume of the insert being the preferred volume. As regards the choice of this solidifiable liquid matrix, it will be selected from liquid solutions, preferably nutritive, capable of taking the form of a solid or a gel under particular conditions compatible with the survival and culture of the cells which make up the skin explant. An example of such a solidifiable liquid matrix is blood plasma, a blood plasma-derived solution (e.g. a dilution of blood plasma in a physiological buffer, in particular a dilution of blood plasma to at least 10%, 20%, 30%, or even at least 40% (weight/total weight of the matrix)), a fibrinogen solution, a collagen solution, a gelatin solution, synthetic polymer solutions, natural polymer solutions (e.g. agarose (low melting point agarose or agar-agar), starch, polysaccharides), and mixtures thereof. Ideally, this solidifiable liquid matrix contains no growth factors, and even better, no serum.

According to a preferred embodiment, the solidifiable liquid matrix is composed of two solutions which are mixed together in the insert prior to the step i) of immersing the skin explant. This matrix is then composed of a first solution selected from a blood plasma solution, a blood plasma-derived solution, a fibrinogen solution, a collagen solution, and mixtures thereof, and a second solution of low melting point agarose or agar-agar.

The first solution, selected from a blood plasma solution, a blood plasma-derived solution, a fibrinogen solution, a collagen solution, or mixtures thereof, is advantageously a nutrient solution. Now, this first solution is mainly able to solidify under the action of an increase or decrease in temperature and/or by the addition of a specific compound or composition. Preferably, the compound allowing this first solution to solidify is the $Ca^{2+}$ ion. Thus, the liquid matrix has a $Ca^{2+}$ concentration between 1 mM and 5 mM, preferably between 1.5 mM and 4.5 mM; which concentration will cause it to solidify.

According to a first particular embodiment, the liquid matrix has a $Ca^{2+}$ concentration between 1 mM and 2 mM, preferably between 1.2 mM and 1.4 mM.

According to a second particular embodiment, the liquid matrix has a $Ca^{2+}$ concentration between 2 mM and 3 mM, preferably between 2.5 mM and 2.9 mM, more preferentially 2.8 mM of $Ca^2$.

It should be noted that in the case of a blood plasma solution or a blood plasma-derived solution, it is first treated with an anticoagulant agent with reversible properties. To this end, this solution comprises at least one anti-fibrinolytic agent, such as sodium citrate, tranexamic acid, or aprotinin, and in sufficient concentration to obtain the desired anti-fibrinolytic activity. Preferably the liquid matrix has a final concentration (weight/total weight of the matrix) between 2 and 5% of this at least one anti-fibrinolytic agent.

Now, the first solution will preferably be a fibrinogen solution.

The second solution of low melting point agarose or agar-agar is previously heated for a time and at a temperature sufficient to be liquid and to remain liquid at about 37° C. for the time sufficient to be mixed with the first solution in said insert and until the skin explant is immersed. Typically, this second solution is preheated to its melting temperature or to a slightly higher temperature, preferably to a temperature between 65° C. and 70° C. The choice of low melting point agarose or agar-agar is made so as to benefit, for a 1.5% (weight/composition total weight) solution, from a gelling temperature between 24° C. and 28° C., and a melting temperature above 65.5° C. By way of example, the agarose called Low Melting Point LMP Agarose (GIBCO-BRL, LIFE TECHNOLOGIES) can be mentioned. Still in connection with this second solution, its concentration in low melting point agarose or agar-agar is between 1% and 5% (preferably in a physiological solution), more preferably between 2% and 5%, between 3% and 4.5%, between 3.5% and 4.5%, or between 3.8% and 4.2%, or between 3.9% and 4.1%, with 4% being the most preferred concentration (by weight relative to the total weight of the composition). At this concentration and once heated to its melting point or a slightly higher temperature, this second solution of low melting point agarose or agar-agar can be stored in liquid form for at least 1 hour at 37°, and ideally for at least 4 hours, 10 hours, or 16 hours. Preferably, the solidifiable liquid matrix comprising said first and said second low melting point agarose or agar-agar solution has a final concentration in low melting point agarose or agar-agar between 0.1% and 2%, preferably between 0.2% and 1.8% (weight/total weight of the matrix). Such a concentration makes it possible to obtain not only a matrix which once solidified makes it possible to preserve the three-dimensional structure and keep said skin fragment or biopsy alive, but also to obtain a matrix which is solid but sufficiently flexible to be non-brittle and resistant to punctual shocks. Said liquid matrix is solidified after laying the skin fragment or biopsy by leaving the device thus obtained at a temperature between 37° C. and the room temperature, preferably 20° C.

According to a first particular embodiment, the final concentration of low melting point agarose or agar-agar in the liquid matrix (comprising the first and said second solution) is between 0.5% and 2%, preferably between 0.5% and 1.25%, more preferably between 0.5% and 1.0%, with a concentration of 0.7% (weight/total weight of the matrix) being the most preferred concentration.

According to a second particular embodiment, the final concentration of low melting point agarose or agar-agar in the liquid matrix (comprising the first and said second solution) is between 0.1% and 2%, preferably between 0.2% and 1.75%, with 0.25% being the most preferred concentration. Such a concentration makes it possible to obtain a matrix which, once solidified, makes it possible both to preserve the three-dimensional structure and keep the skin explant alive, and simultaneously obtain a matrix which is sufficiently flexible to be non-brittle and sufficiently resistant to mechanical effects applied to the skin explant. This liquid matrix is solidified after immersing the skin explant by allowing the assembly to cool down.

According to another preferred embodiment, the solidifiable liquid matrix further comprises cells other than the cells that make up the skin explants, which cells are selected from the group consisting of fibroblasts, endothelial cells, and nerve cells. Preferably, these cells are fibroblasts, and ideally primary fibroblasts (as opposed to fibroblast cell lines), such as dermal fibroblasts obtained from human foreskin. These primary, especially dermal, fibroblasts, can be prepared and obtained from standard methods well known to the one skilled in the art (see for example the document HOWARD B V et al., *A new method for the establishment of diploid fibroblast cell cultures from human foreskins*, Proc. Soc. Exp. Biol. Med., vol. 153(2), p:280-3, 1976). Preferably, these cells, and especially the fibroblasts, are contained in the matrix at a concentration between $5 \cdot 10^3$ and $5 \cdot 10^5$ cells/ml, preferably still between $10^4$ and $10^5$ cells/ml, with the range $3 \cdot 10^4$ to $5 \cdot 10^4$ cells/ml being the most preferred concentration range.

In addition, the liquid matrix may comprise various compounds such as preservatives, pH agents, etc. By way of example, the liquid matrix will contain between 5 and 500 mg/mL of ascorbic acid, preferably between 25 and 75 mg/mL, with a preferred ascorbic acid concentration of 50 mg/mL.

According to a third, also preferred, embodiment, the solidifiable liquid matrix is a blood plasma-derived solution and comprises:
  a) 25 to 75% (volume/total volume$^{4*}$) of fibrinogen, preferably 35% to 45% (v/v),
  b) 5% to 12% (volume/total volume) of a 1% $CaCl_2$) saline solution, preferably 8%,
  c) 5% to 2%, preferably of the anti-fibrinolytic agent, preferably said anti-fibrinolytic agent being selected from tranexamic acid or aprotinin
  d) 0.5% to 4% of low melting point agarose, preferably 1% to 2%, and
  e) a physiological solution such as a 0.9% NaCl solution, q.s. 100%.

For more details on solidifiable matrices and methods for placing skin explants therein, please refer to European patent application No. EP 2 882 290 A1. Now, these matrices and methods are incorporated into this patent application by reference.

As regards the insert, it can take multiple forms and in particular it can correspond to a suspended insert or an insert on stilts. Now, a suspended insert will be preferably used. The bottom of this insert consists of a porous membrane, the diameter of which is between 5 and 40 mm, and more preferably between 9.5 and 30 mm. As regards the porosity of this membrane, it must be such as to prevent the liquid matrix from passing through it before it solidifies. Typically, this porous membrane will have a porosity between 0.4 and 8 µm, preferably between 0.4 µm and 1.5 µm, with the range 0.8 µm to 1.2 µm being the preferred porosity range. In terms of material, a porous membrane selected from polyethylene terephthalate (PET), nitrocellulose, and polycarbonate membranes can be used. Finally, and by way of example of such inserts, those supplied by the companies NUNC, CORNING, BECTON DICKINSON (BD FALCON), MILLIPORE (MILLICELL), which can take the form of inserts with polycarbonate, PET, or nitrocellulose membrane, which are pre-packaged in multi-well plates for 6, 8, 12, or 24-well culture plates, and the membrane porosity of which can vary from 0.4 to 8 µm, can be mentioned. Typically, the inserts used have a PET membrane with a porosity between 0.8 µm and 1 µm, and are suitable for the wells of 8-well culture plates.

The step of solidifying the liquid matrix is carried out in the presence of calcium ions, preferably also in the presence of thrombin. When the liquid matrix is a liquid matrix containing a blood plasma solution, a blood plasma-derived solution, a fibrinogen solution, or a collagen solution, the solidification of this matrix in step ii) is obtained for this solution following the addition of thrombin and/or following an increase in temperature and/or in the presence of factors secreted by the cells such as primary fibroblasts integrated into the matrix. Advantageously, this liquid matrix solidifies after a maximum of 8 hours, preferably less than one hour, with a preferred duration of the solidification step of less than 10 min after immersion of the skin explant in the solidifiable liquid matrix in step i).

Advantageously, the method according to the invention further comprises the steps of:
  iii) placing the insert in a container or culture well, and
  iv) culturing the skin explant in an appropriate medium.

Typically, the container or well in which this insert is deposited is a well of a cell culture plate with 6, 8, 12, 24, or 48 wells. Among the culture plates that can be used in the method according to the invention are those supplied in particular by the companies NUNC, CORNING, BECTON DICKINSON (BD FALCON), MILLIPORE (MILLICELL).

According to another preferred embodiment, the bottom of the insert is located at a distance between 1 and 2.5 mm from the bottom of the container/well containing it.

The method according to the invention may, furthermore, comprise a step iii'), following step iii), which consists in affixing a cover or film to the container or well in which the insert was placed in step iii), with a view to making this container or well watertight. In this way, the resulting container or well can be transported without difficulty, whether by land, sea, or air. Indeed, the skin explant is not only trapped and hence held firmly by the solid matrix in the insert with a porous membrane, but also nourished, being able to travel without a culture medium during transport while being kept alive.

By "culture" or "culturing" is meant here, in particular, keeping the physiological state and, where appropriate, the morphological state of the skin explant, and therefore of said cells forming it. Thus, the aim of this step is to limit cell death phenomena and to maintain the state of differentiation of the cells (in fact to limit inappropriate dedifferentiation or differentiation phenomena).

By "medium" or "culture medium" is meant a liquid composition comprising all the elements necessary for the culture of skin explant cells (e.g. William's E medium, KBM, DMEM, etc.). This culture medium, by its nature as much as by its volume in the container, helps to promote the survival of the skin explant and the cells that make it up over time. In addition to the survival of the cells of the skin explant, the culture medium in question makes it possible, in particular by limiting the stress thereon, to maintain the cells of the skin explant in their initial state, whether in structural or functional terms.

In the case where the method according to the invention does not comprise step iii') described above, it could comprise a step iv'), following step iii), which consists in affixing a cover or film to the container or well in which the insert was placed in step iii), with a view to making this container or well watertight. In this way, the container or well obtained can be transported without difficulty, whether by land, sea, or air.

According to a preferred embodiment, the method according to the invention further comprises the step of:
  v) injecting, subcutaneously and in the skin explant, a composition.

The composition in question is a test composition which is in liquid form. Advantageously, the volume of this composition is between 10 µl and 1 ml, preferably between 10 µl and 500 µl, and particularly preferably between 10 µl and 200 µl.

The needle for injection of the composition typically has sufficient length to reach the hypodermis. Thus, needles with a length of 10 mm or more are preferably used. By way of example of such needles, needles with a length of 12, 16, 20, 25, 30, 35, 40, or even 45 mm may be used. Advantageously, the needle thus has a length between 16 and 45 mm, preferably a length between 20 and 40 mm. As far as the diameter of the needle to be used is concerned, it can be identified simply by the one skilled in the art with regard to his/her general knowledge. Typically, such hypodermic needles are 18 G-, 19 G-, 20 G-, 21 G-, 22 G-, 23 G-, 25 G-, 26 G-, 27 G-, 28 G-, 29 G-, 30 G-, or even 31 G-type needles.

In a particular embodiment, step v) is carried out by an experimenter. In such a case, the injection step v) may be directly preceded by a step v°) of pinching the skin explant by the experimenter so as to allow the formation of a skin fold and to facilitate, for the experimenter, the subcutaneous injection step v).

In another particular embodiment, this step v) is carried out by an automatic injection device. Typically, the device allows an injection at a certain depth, relative to the surface of the epidermis, so that a subcutaneous injection is obtained.

According to another preferred embodiment, the method according to the invention further comprises the step of:
  vi) determining the injectability of the composition.

When the injection step v) is carried out by an experimenter, he/she will determine the injectability of this composition. To do so, it is possible to associate this injectability with arbitrary values associated with specific characteristics of this injection. By way of an example, the experimenter could use the scale below:

Score 1: injection impossible or very difficult; flow: nil or slow (surges)
Score 2: difficult injection; flow: slow at the beginning (surges), and then continuous
Score 3: correct injection; flow: continuous
Score 4: easy injection; flow: continuous The experimenter, by injecting the given composition several times, can assign it an average injectability value.

When the injection step v) is now carried out by an automatic injection device, the injectability is determined thereby. To do this, the automatic injection device is coupled to a dynamometer. Thus, the automatic injection device is able to determine the force required (mPa) for subcutaneous injection of the composition.

More specifically, the dynamometer makes it possible to determine:
  1) the initial glide force ("initial glide force" or PBF), which corresponds to the force required to move the syringe plunger;
  2) the maximum force (Fmax) which corresponds to the largest measured force value for moving the syringe plunger before the syringe plunger completes its stroke at the end of the syringe; and/or
  3) the dynamic glide force ("dynamic glide force" or DGF), which corresponds to the force required to keep the syringe plunger moving so that it expels the contents thereof.

These three values are characteristic of the injectability of a composition.

Now, and according to another preferred embodiment, the method according to the invention may comprise a step of:
  vi) determining the injection bolus of the composition, with the local toxicity resulting from the injection of the composition and/or the efficacy of the composition.

In connection with the knowledge of the therapeutic dose to be administered, the method according to the invention makes it possible to truly determine the injection bolus by selecting a volume of a composition which has a given concentration of an active ingredient.

Likewise, the method according to the invention makes it possible to access the local toxicity resulting from the injection. This can be done by carrying out morphological and/or molecular analysis at the injection site. Such an analysis can be carried out by embedding the ex vivo skin model following injection, preparing sections from the block obtained, and finally visually and/or immunohistochemically analyzing the sections located at the injection site.

Finally, as regards the determination of the efficacy of the composition, this is only possible if the therapeutic effect resulting from the composition can be determined at the level of the ex vivo injection model.

As regards the second object of the invention, it is a cell culture insert obtainable at the end of step ii) of the method according to the invention.

Now, it may be the insert as obtained at the end of step iii') of the method according to the invention.

All the specific features of this insert are described above and in particular the fact that it can take multiple forms such as a suspended insert or a insert on stilts with a preference for a suspended insert thanks to the presence of lugs (60). This insert may in particular consist of a porous membrane, the diameter of which is between 5 and 40 mm, in particular between 9.5 and 30 mm, the porosity of which is between 0.4 and 8 µm, or even between 0.4 µm and 1.5 µm, and which is selected from polyethylene terephthalate (PET), nitrocellulose, and polycarbonate membranes.

In connection with the third object of the invention, it is more specifically the determination of the injectability of a given composition that is targeted. Naturally, this injectability depends not only on the composition, but also on the syringe and especially on the needle used.

Finally, a kit comprising an insert as defined above and an automatic injection device, which is preferably coupled to a dynamometer, so as to be able to determine the injectability characteristics of a composition. Preferably, the automatic injection device is able to determine the initial glide force (PBF), the maximum force (Fmax), and the dynamic glide force ("dynamic glide force" or DGF) of the composition.

The following examples are given solely by way of illustration of the subject matter of the present invention, and in no way constitute a limitation thereof.

EXAMPLES

1) Stability of the Explant Over Time

Skin explants are prepared from two complete skin specimens from two separate donors, which specimens comprise the epidermis, dermis, and hypodermis (1.5 to 2 cm). The explants (epidermis, dermis, and hypodermis) are then cut out using a metal punch to obtain cylinders 11 to 20 mm in diameter in which the thickness of the hypodermis is adjusted to the desired value (0.5 to 1 cm). They are then kept floating in a buffered saline solution until the stage of "embedding" into the solidified matrix.

Each skin explant is then embedded with a method similar to the one used for the NATIVESKIN™ model. Briefly, the skin explant is laid delicately on an insert (MILLICELL™ 8-well cavity) with a porous membrane (made of PET, 1 μm porosity) at the bottom, containing a blood plasma-derived solution treated with an anticoagulant agent with reversible properties in the presence of calcium ions (sodium citrate). This solution contains 42% blood plasma, 50% of a 0.9% NaCl solution, 8% of a 1% $CaCl_2$) salt solution, an anti-fibrinolytic agent (tranaxemic acid or aprotinin), and 0.7% low melting point melted agarose (Agarose LMP GIBCO-BRL, LIFE TECHNOLOGIES) (melted in a stove at 65.5° C.).

By coagulating, the plasma acts as a dermal support on which the skin explant adheres. The coagulation mainly consists of the transformation, in the presence of calcium ions and thrombin, of the fibrinogen present in the plasma into a scaffolding of fibrin molecules linked together by covalent bonds. The function of the anti-fibrinolytic agent is to inhibit the enzymes capable of degrading the plasma matrix, with said enzymes being secreted by the skin explant, and thus to maintain the integrity of the explant.

The 0.7% agarose solution contained in the plasma solution gradually gels at 37° C., thereby holding the skin explant firmly in the insert.

FIG. 1 shows such a cell culture insert (1) with lugs (5), the bottom of which consists of a porous membrane (2) and which contains the skin explant (3) after it has been trapped in the solidified matrix (4).

The assembly of the skin explant is kept in culture for 7 days in a $CO_2$ incubator at 37° C. with the epidermis in contact with air. The DMEM culture medium supplemented with calcium and vitamin C contained in the insert placed (suspended) on the well of the cell culture plate is changed daily.

For both donors, skin explants are taken at D0, D3, and D7 days of culture before being fixed and embedded in a paraffin block for histological analysis.

In detail, the skin explants are dehydrated by a first alcohol bath, and then by a second xylene bath. Finally, a first bath in paraffin allows to replace the water previously contained in the skin explant by paraffin. The paraffin-impregnated samples are removed from their bath and transferred to a container, the bottom of which is lined with absorbent paper, to be taken to the vicinity of the embedding station.

The samples, enclosed in histology cassettes, are immersed in liquid paraffin at 56° C. to again melt the paraffin impregnating them.

For each sample, the histology cassette is opened, the sample is possibly cut in half. An embedding mold is filled with liquid paraffin, and the sample (or the 2 sample pieces) is placed in the mold and oriented in the desired direction for cutting. At the same time, the mold is transferred onto a refrigerated rack in order to solidify the paraffin at the bottom of the mold and hold the sample therein. The lid of the histology cassette with the sample reference placed on top is placed thereover, so that the paraffin passes therethrough (paraffin can be added if necessary), and then the assembly is placed in cold storage (refrigerator, freezer, cold room . . . ) for several minutes (5 to 6), in order to solidify the paraffin into a block, thus trapping the sample in the right orientation with the lid of the histology cassette which will become the support of the block.

Once the block has solidified, it is released from the mold. Excess paraffin is possibly scraped off with a spatula on the sides of the lid of the embedding cassette.

Serial sections of a thickness varying from 4 to 5 μm are then made along the entire length of the paraffin block containing the sample.

Figure 2A:
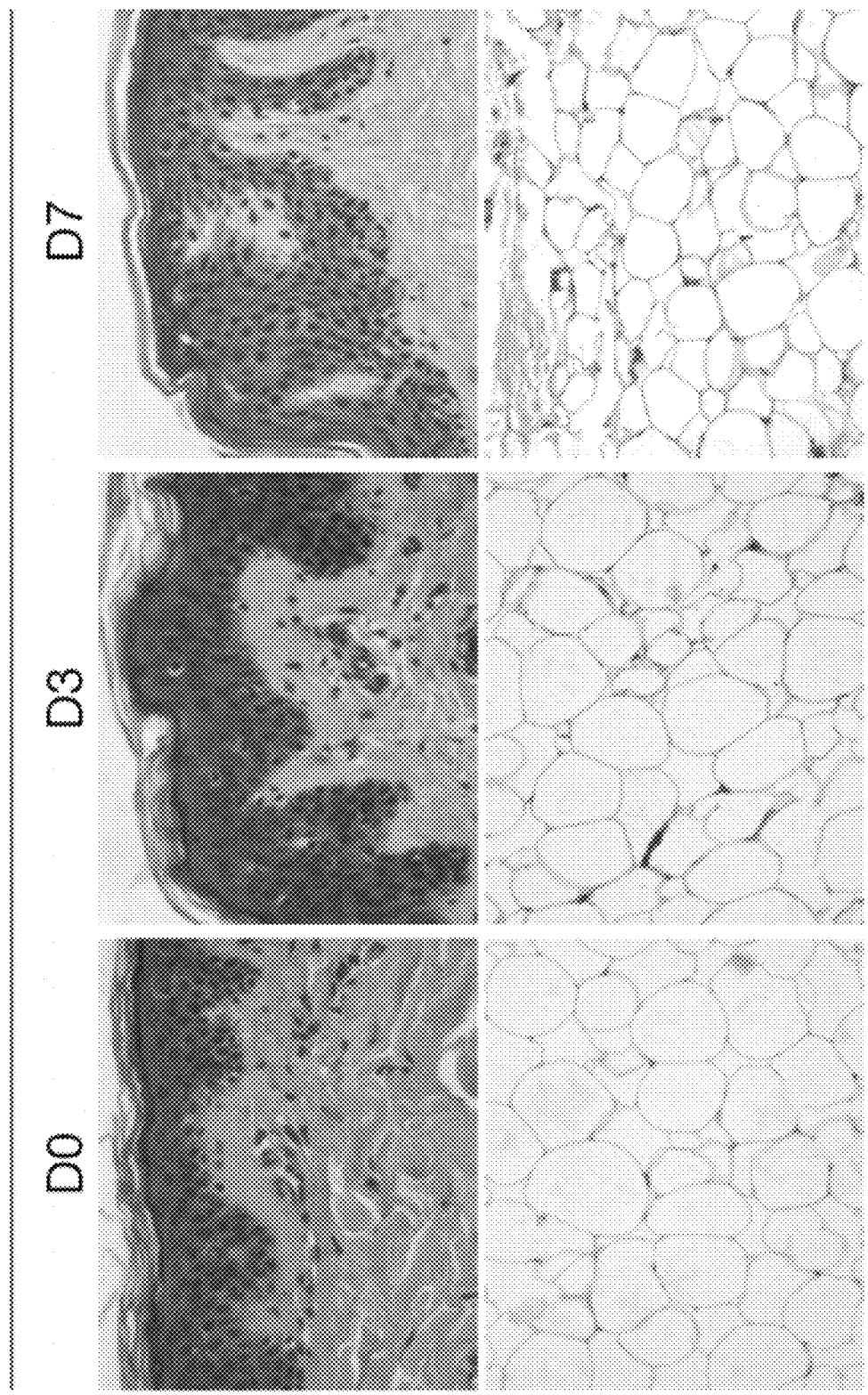
FIGS. 2A and 2B show sections of skin explants from two separate donors used in the method according to the invention at 0, 3, and 7 days of culture.
Figure 2B:
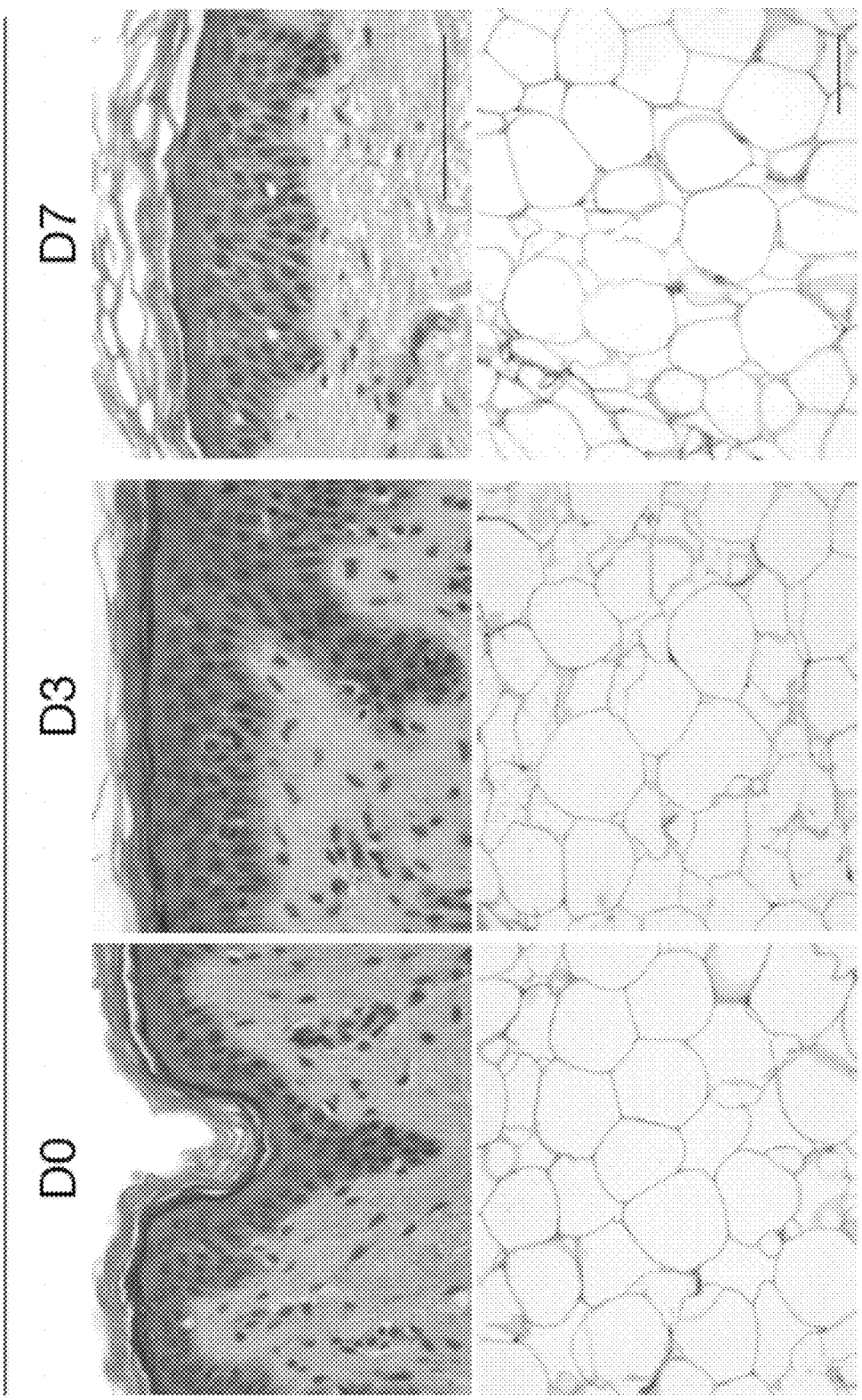

FIGS. 2A and 2B illustrate the results of staining performed (Hematoxylin and Eosin) on the skin explants from two separate donors used in the method according to the invention after 0, 3, or 7 days of culture.

The results show a remarkable stability of the explants over time both in terms of structure (the different layers of the skin, including the hypodermis, show no noticeable change) and viability (no significant cell death is observed).

To refine this analysis, the evolution of adipocytes was followed over time by image analysis (ADIPOSOFT PLUGIN of the freeware IMAGEJ).

Figure 3:
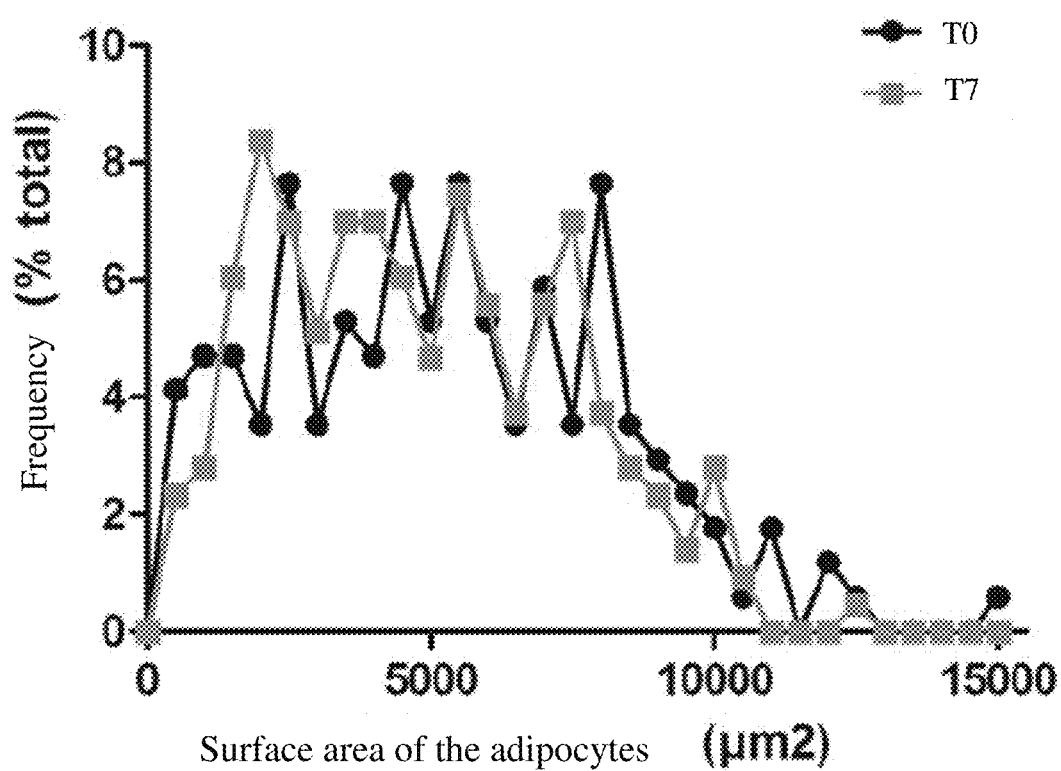
FIG. 3 illustrates the stability over time of adipocyte size within the skin explant in the ex vivo model for subcutaneous injection.

FIG. 3 shows the distribution of adipocytes depending on their surface area in the different explants at 0 and 7 days of culture.

Here again, the results establish the high stability over time of the adipocytes within the skin explant of the ex vivo model for subcutaneous injection.

Finally, these results show that the skin explant has a stable structure of its hypodermis (as well as its dermis and epidermis) over time, making it an ex vivo model of complete skin.

2) Subcutaneous Injection

Skin explants are prepared as before.

Various tests carried out on cultured skin explants show that subcutaneous injections can be performed without difficulty on these skin explants. In addition, and as long as the explant has a suitable diameter (of the order of . . . mm), it is easy to make a skin fold with a fine clamp, so as to carry out this injection. Under these conditions, the explant holds perfectly and behaves exactly like an individual's skin.

In order to establish that the skin explant is indeed an ex vivo model for subcutaneous injection, we investigated whether the skin explant reacted in the same way as in vivo.

To this end, 100 μL of a pro-inflammatory solution consisting of TNF-alpha (500 ng/mL) and LPS (0.2 mg/mL) was injected into the adipose tissue of the models using a syringe and a 12 mm long 27 G needle. The models were then cultured under cell culture conditions (incubator at 37° C., 5% $CO_2$, and water-saturated atmosphere for 6 h, 12 h, or 24 h.

Figure 4:
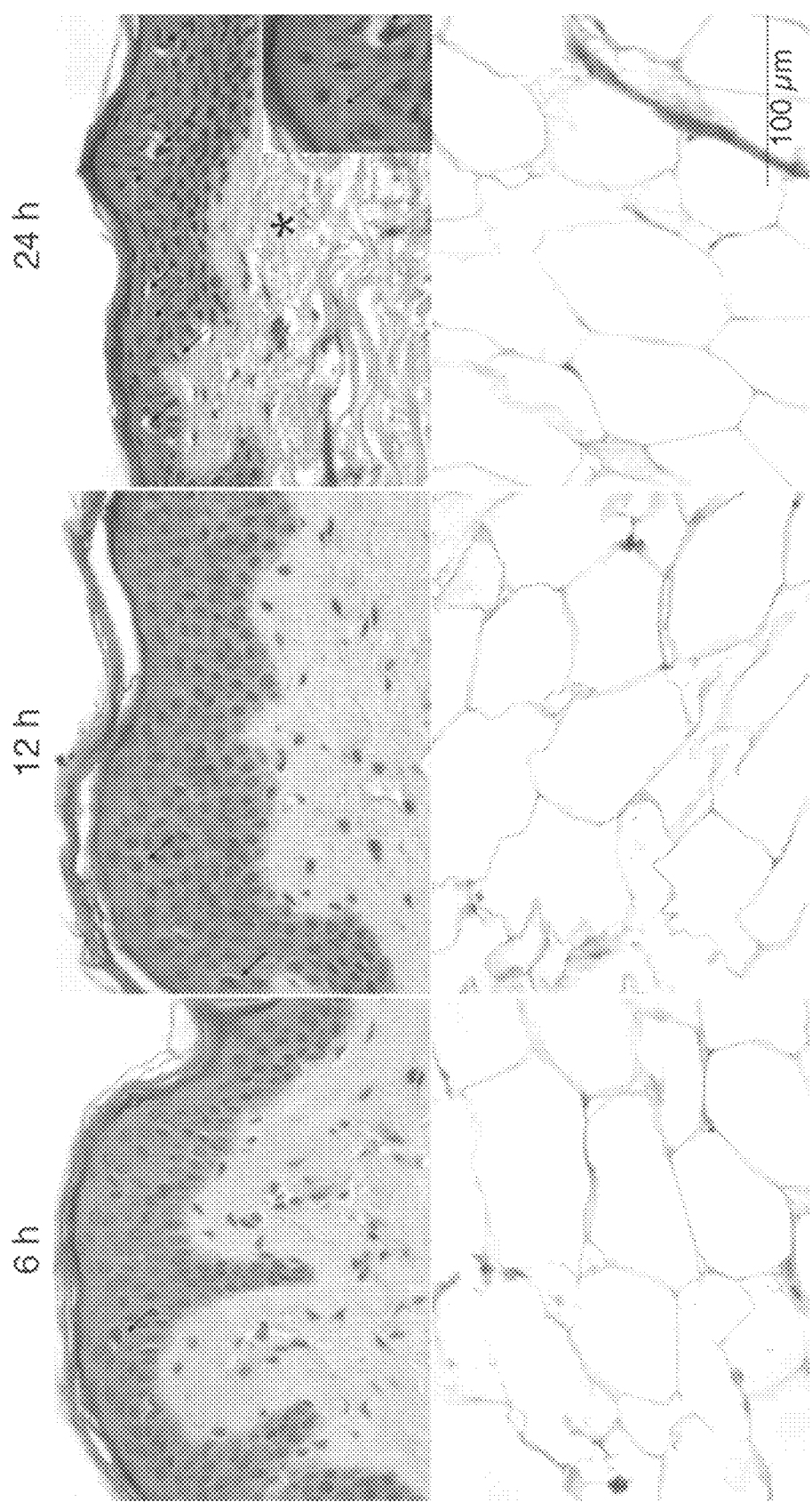
FIG. 4 shows sections of skin explants 6 h, 12 h, and 24 h after injection of a pro-inflammatory cocktail into the adipose tissue.

FIG. 4 shows H&E staining performed on 5 μm thick paraffin sections to evaluate the effect of the injected solution on tissue viability and structure.

The results show the appearance of vacuolized and pycnotic cells in the epidermis of the models, as well as partial degradation of the collagen fibers of the dermis, suggesting degeneration linked to the effect of the pro-inflammatory solution.

Consequently, these results confirm the relevance of this subcutaneous injection model, which indeed behaves like skin in vivo.

The invention claimed is:

1. An in vitro method for modelling subcutaneous injection comprising the steps of:
   i) immersing a skin explant in a solidifiable liquid matrix such that an upper face of an epidermis of the skin explant is not covered, wherein the matrix is contained in a cell culture insert, the bottom of which consists of a porous membrane,
   ii) solidifying the matrix so as to trap the immersed portion of the skin explant, wherein the upper face of the epidermis is not covered, and adhering the matrix to side walls and the porous membrane of the insert,
   iii) placing the insert in a container or a culture well, and
   iv) culturing the skin explant in a medium, wherein the skin explant comprises a thickness of at least 5 mm of a hypodermis and wherein the method further comprises the step of
   v) injecting a composition in the hypodermis of the skin explant.

2. The method of claim 1, wherein said method further comprises the step of:
   vi) determining the injectability of the composition.

3. The method of claim 2, wherein said method further comprises the step of:
   vi) determining an injection bolus of the composition, with local toxicity resulting from the injection of the composition and/or the efficacy of the composition.

4. A cell culture insert that is an ex vivo model for subcutaneous injection, which can be placed in a container or culture well comprising:
   a bottom consisting of a porous membrane, and
   a skin explant trapped in a solidified matrix which is in contact with an inner edge of the insert and the porous membrane, the skin explant comprising an epidermis, a dermis, epidermal appendages and a hypodermis and
   wherein the epidermis of the skin explant is in contact with the atmosphere, and the dermis, epidermal appendages, and the hypodermis of the skin explant are immersed in the solidified matrix and
   wherein the hypodermis of the skin explant comprises a thickness of at least 5 mm.

5. A kit comprising:
   a cell culture insert that is an ex vivo model for subcutaneous injection, which can be placed in a container or culture well,
   the cell culture insert having a bottom consisting of a porous membrane, and a skin explant trapped in a solidified matrix which is in contact with an inner edge of the insert and the porous membrane, the skin explant comprising an epidermis, a dermis, epidermal appendages and a hypodermis;
   wherein the epidermis of the skin explant is in contact with the atmosphere, and the dermis, epidermal appendages, and the hypodermis of the skin explant are immersed in the solidified matrix and
   wherein the hypodermis of the skin explant comprises a thickness of at least 5 mm. and an automatic injection device.

* * * * *